United States Patent [19]
Boaz

[11] Patent Number: 6,096,929
[45] Date of Patent: Aug. 1, 2000

[54] PROCESS FOR THE PREPARATION OF THIOETHER-SUBSTITUTED AROMATIC KETONES

[75] Inventor: Neil W. Boaz, Kingsport, Tenn.

[73] Assignee: Eastman Kodak Company, Kingsport, Tenn.

[21] Appl. No.: 09/369,300

[22] Filed: Aug. 6, 1999

Related U.S. Application Data

[63] Continuation of application No. 09/088,778, Jun. 2, 1998.
[60] Provisional application No. 60/048,758, Jun. 3, 1997.
[51] Int. Cl.$^7$ ................................................ C07C 205/00
[52] U.S. Cl. .......................................... 568/316; 568/306
[58] Field of Search ..................... 568/316, 306

[56] References Cited

U.S. PATENT DOCUMENTS

| | | | |
|---|---|---|---|
| 3,845,133 | 10/1974 | Cohen | 260/586 |
| 5,344,992 | 9/1994 | Drewes et al. | 568/314 |
| 5,502,256 | 3/1996 | Hagedorn et al. | |

FOREIGN PATENT DOCUMENTS

| | | |
|---|---|---|
| 714 046 | 9/1968 | Belgium . |
| 0 470 856 A1 | 2/1992 | European Pat. Off. . |
| 0 658 544 A1 | 6/1995 | European Pat. Off. . |
| 224 589 C | 7/1910 | Germany . |
| 1 618 442 | 12/1970 | Germany . |
| 95/00476 | 1/1995 | WIPO . |
| 97/28122A | 8/1997 | WIPO . |

OTHER PUBLICATIONS

CA:104:148709 abs of Tetrahedron Lett by Danikiewicz 26(30) pp3599–600, 1985.
Chemical Reviews vol. 55 pp 137–155 pp 137–155 "The Nef Reaction" by Noland, 1955.
Reid et al., "Addition of Nitroalkanes to Ortho–Halo–Nitrobenzenes, A New Synthesis of 4–Chloro–7–(Trifluoromethyl) Quinoline", *Tetrahedron Letters*, vol. 31, No. 8, pp. 1093–1096, 1990.
Kirillov et al., "Substitution of the Chlorine Atom in 2,4–Dinitro–Chlorobenzene by the 2–R–5–Nitro–1, 3–Dioxanyl Residue," translated fron *Zhurnal Organicheskoi Khimii*, vol. 23, No. 3, pp. 585–588 (1987).
Bretherick, L., "Bretherick's Handbook of Reactive Chemical Hazards; Fourth Edition", Butterworths, pp. 1693–1694 (1990).
Danikiewicz et al., "Direct Nitromethylation of Nitroaphthalene and its Heteroanalogues, A New Method for Functionlization of Nitroarenes", *Tetrahedron Letters*, vol. 26, No. 30, pp. 3599–3600 (1985),.

Olah et al., "Synthetic Method and Reactions; 89. Improved Transformation of Nitro Compounds into Carbonyl Compounds by Hydrogen Peroxide/Potassium Carbonate", *Synthesis*, pp. 662–663 (1980).
Evans, T.L., "Phase Transfer Catalyzed Melt Synthesis of Diaryl Sulfide", *Synthetic Communications*, 14(5), pp. 435–443 (1984).
Brunelle, D.J., "Preparation of Alkyl Aryl Sulfides via Phase–Transfer Catalyzed Displacement of Aromatic Chloride by Alkyl Thiolates", *J. Org. Chem.*, vol. 49, pp. 1309–1311 (1984).
Degani et al., "S,S–Dialkyl Dithiocarbonates as a Convenient Source of Alkanethiolate Anions in Phase–Transfer–Catalysis Systems: An Improved Synthesis of Organic Sulfides", *Synthesis*, pp. 630–632 (1983).
Reeves et al., "Phase Transfer Catalysis Preparation of Aryl Thioethers", *Synthetic Communications*, vol. 12, No. 13, pp. 1071–1079 (1982).
Landini et al, "Nucleophilic Aromatic Substitution Reactions under Phase–Transfer Conditions. Synthesis of Alkyl Aryl Sulfides from Isomeric Dichlorobenzenes and Thiolates," *J. Org. Chem.*, vol. 48, pp. 604–605 (1983).
Shner et al., "Phase–Transfer Catalysis of the Reduction of Aromatic Nitro Compounds with Sodium Sulfide", *Zhurnal Organicheskoi Khimi*, vol. 25, No. 4, pp. 879–880 (1989).
Coombes et al., "On the Synthesis of 2–methylchromene–4–thione and 2–methyl–1–thiochromone", *Phosphorous and Sulfur*, vol. 14, No. 2, pp. 139–142 (1983).
March, Jerry, "Advanced Organic Chemistry", John Wiley & Sons, Eds. New York, pp. 886–887 (1992).
Bartlett, et al., "A Mild, Oxidative Nitro–to Carbonyl Conversion and a New Prostaglandin Synthon", *Tetrahedron Letters*, No. 4, pp. 331–334 (1977).

*Primary Examiner*—Johann Richter
*Assistant Examiner*—Jean F Vollano
*Attorney, Agent, or Firm*—Michael J. Blake, Esq.; Harry J. Gwinnell

[57] ABSTRACT

The preparation of aromatic ketones substituted with a thioether group at the ortho position is accomplished by the initial reaction of an aromatic nucleus substituted with a halide and an ortho nitro group with a nitroalkane in the presence of a hydroxide base. The resulting ortho-nitroalkyl nitroarene compound is converted to the corresponding ortho-nitroaryl ketone by an oxidative Nef reaction. The aromatic nitro group of the ortho-nitroaryl ketone is replaced with a thioether group by reaction with a thiolate anion, most preferably under phase-transfer conditions. Aromatic ketones may be used to prepare various pharmaceutical and herbicidal compounds.

7 Claims, No Drawings

PROCESS FOR THE PREPARATION OF THIOETHER-SUBSTITUTED AROMATIC KETONES

This is a continuation of application Ser. No. 08/088,778 filed on Jun. 2, 1998, which claims the benefit of U.S. Provisional Application Ser. No. 60/048,758, filed Jun. 3, 1997 each of which is incorporated in its entirety by reference.

This application claims under 35 U.S.C. 119(e) the benefit of U.S. Provisional Application No. 60/048,758, filed June 3, 1997, which is incorporated in its entirety by reference.

BACKGROUND OF THE INVENTION

1. Field of the Invention

The invention relates to a process for the preparation of ortho-thioether-substituted aromatic ketones. More preferably, the invention relates a process of preparing an ortho-thioether-substituted aromatic ketone from a halonitroarene compound having a halo group ortho to a nitro group. Aromatic ketones are useful synthetic reagents for the preparation of both industrially important compounds such as herbicides and pharmaceutical compounds such as antihypertensive agents.

2. Description of the Related Art

Aromatic ketones are important synthetic intermediates for a number of valuable chemical compounds. For example, such compounds include isoxazole and isoxazole derivatives (Casado et al., WO 95/00476; and Cain et al., EP 470856). These compounds are useful herbicides. These types of ketones are normally prepared by the Friedel-Crafts acylation of an aromatic nucleus. However, in some cases these methodology does not produce the desired isomer, and more indirect methods must be employed.

Preparation of aromatic ketones via a nitroalkane displacement of a chloronitroarene followed by an oxidative Nef reaction has been previously reported. Such aromatic ketones are shown to be useful as synthetic intermediates in the preparation of antihypertensive agents. Reid et al., *Tetrahedron Lett.* 31:1093 (1990). That preparation, however, utilizes the expensive base, diazabicyclo[2.2.1]undecene, for the displacement step. A similar reaction has been reported involving the displacement of 2,4-dinitrochlorobenzene by the lithium salt of 5-nitro-1,3-dioxane in DMSO solution. Kirillov et al., *Zh. Org. Khim.* 23:585 (1987). In this case, the nitronate salt was prepared and isolated in dry form from 5-nitro-1,3-dioxane and lithium methoxide in a separate reaction, a dangerous process due to the explosive nature of many alkanenitronate salts. Bretherick, L., *Bretherick's Handbook of Reactive Chemical Hazards; Fourth Edition*, Butterworths, London, 1693 (1990). This methodology is also not viable when using primary nitroalkanes unless additional base is used, since the displacement product is more acidic than the nitroalkane reactant. Unfortunately, the use of additional alkoxide base is not feasible either since commercially available alkoxide bases act primarily in a nucleophilic manner, affording as the major product the alkyl ether derived from aromatic nucleophilic displacement by the alkoxide.

The addition of nitromethane to nitroarenes using sodium hydroxide in dimethyl sulfoxide has been reported. Danikiewica et al., *Tetrahedron Lett.* 26:3599 (1985). This is a mechanistically different type of reaction than the nucleophilic aromatic substitution reaction, as it is an addition followed by aromatization (oxidation). The yields are quite low and the reaction works only with bicyclic nitroarene compounds and not with monocyclic nitroarene substrates.

Classic Nef reactions are performed by adding a solution of a nitronate anion to a strongly acidic aqueous solution. However, in many cases these conditions achieve only minimal conversion of the nitro group to the corresponding ketone, especially with a nitronate anion substituted on an aromatic ring. Conversion to the desired ketone can be achieved under oxidative Nef reaction conditions. However, a large excess of hydrogen peroxide, which is hazardous and economically unattractive, is necessary. Olah et al., *Synthesis* 662 (1980).

Phase-transfer catalyzed aromatic nucleophilic displacements by thiolates have been reported, but none of these involve aromatic nitro groups as the leaving group. EP 658544 (1995); Evans T. L., *Synth. Commun.* 14:435 (1984); Brunelle, D. J., *J. Org. Chem.* 49:1309 (1984); Degani et al., *Synthesis* 630 (1983); Reeves et al., *Synth. Commun.* 12:1071 (1982); and Landini et al., *J. Org. Chem.* 48:604 (1983).

Accordingly, there exists a need in the art for an efficient and cost-effective process for preparing aromatic ketones not accessible via classical Friedal-Crafts chemistry. There also exists a need for an efficient and cost-effective route to ortho-thioether-substituted aromatic ketones.

SUMMARY OF THE INVENTION

The invention provides a straightforward, efficient and cost-effective process for the preparation of aromatic ketones having a nitro group ortho to a keto group. The process contacts a halonitroarene compound having a halo group ortho to a nitro group with a nitroalkane in the presence of a hydroxide base in a polar aprotic solvent to produce an ortho-nitroalkyl nitroarene compound. The process then oxidizes the ortho-nitroalkyl nitroarene compound to a corresponding aryl ketone having a nitro group ortho to a keto group.

The invention also provides a process for the preparation of ortho-thioether-substituted aromatic ketones. The process contacts an ortho-nitroaryl ketone with a thiolate anion, optionally in the presence of a catalyst, to produce an ortho-thioether-substituted aromatic ketone.

The invention further provides a process for the preparation of an ortho-thioether-substituted aromatic ketone from an ortho-nitro haloarene compound. The process first contacts a halonitroarene compound having a halo group ortho to a nitro group with a nitroalkane in the presence of a hydroxide base in a polar aprotic solvent to produce an ortho-nitroalkyl nitroarene compound. The ortho-nitroalkyl nitroarene compound is then oxidized to produce an ortho-nitroaryl ketone. Contacting the ortho-nitroaryl ketone with a thiolate anion, optionally in the presence of a catalyst, produces an ortho-thioether-substituted aromatic ketone. The process can be performed without isolation of either the ortho-nitroalkyl nitroarene compound or the ortho-nitroaryl ketone.

The invention, accordingly, also provides for reaction product mixtures produced as a result of each process step.

DETAILED DESCRIPTION OF THE INVENTION

One embodiment of the invention is a process for the preparation of an aromatic ketone having a nitro group ortho to a keto group. The process contacts a halonitroarene compound having a halo group ortho to a nitro group with a nitroalkane in a polar aprotic solvent and in the presence of a hydroxide base to produce an ortho-nitroalkyl nitroarene compound. The process also involves oxidizing the ortho-nitroalkyl nitroarene compound to produce an ortho-nitroaryl ketone. This process, along with preferred embodiments, is described in more detail in the following discussion and examples.

The first step of this process is a substitution reaction of a halonitroarene compound of formula (1) where the halo group is ortho to the nitro group:

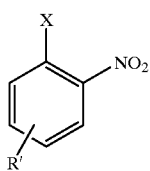

(I)

In formula (1), X is a halide selected from the group consisting of fluorine, chlorine, bromine and iodine and R' is a substituted or unsubstituted $C_1$–$C_{10}$ alkyl, $C_6$–$C_{10}$ aryl, or $C_4$–$C_{10}$ heteroaryl group, preferably having electron withdrawing properties. Unless indicated otherwise, an alkyl group as used throughout refers to a straight chain or branched hydrocarbon group. Preferably, the alkyl group is a $C_1$–$C_5$ alkyl group. An aryl group as used throughout refers to an aromatic group while a heteroaryl group as used throughout refers to an aromatic group containing at least one heteroatom. Possible heteroatoms for the heteroaromatic groups include nitrogen, oxygen, and sulfur. Preferred aryl or aromatic groups and heteroaryl or heteroaromatic groups include, but are not limited to, phenyl, furanyl, pyrrolyl, isopyrrolyl, thienyl, napthyl, pyridinyl, and pyranyl. Possible substituents include, but are not limited to, alkyl, aryl, heteroaryl, ether, thioether, halo, nitro and other similar groups. Preferably, X is chlorine or bromine and R' is an electron withdrawing group such as trifluoromethyl. When R' is an aryl group, the ortho-nitrohaloarene may also have a fused aromatic ring structure such as anthracene or naphthalene.

According to the invention, the process contacts the ortho-nitrohaloarene with a nitroalkane of the formula (Ia):

$O_2N$—$CH_2$—$R$ (Ia)

In formula (Ia), R is a substituted or unsubstituted $C_1$–$C_{10}$ alkyl, $C_6$–$C_{10}$ aryl, or $C_4$–$C_{10}$ heteroaryl, each as described above. More preferably, R is a methyl group.

The reaction between the ortho-nitrohaloarene (I) and the nitroalkane (Ia) takes place in the presence of a hydroxide base in a polar aprotic solvent to afford an ortho-nitroalkyl nitroarene compound of formula (II):

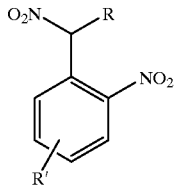

(II)

where R and R' are as defined above. Unexpectedly, the combination of a hydroxide base in a polar aprotic solvent promotes and maximizes formation of an ortho-nitroalkyl nitroarene compound of formula (II) and minimizes formation of the hydrolysis product.

In the substitution reaction, the base may be any hydroxide base. Examples of such bases include, but are not limited to, alkali metal hydroxides and alkaline earth metal hydroxides. Preferably, the base is an alkali metal hydroxide, such as sodium hydroxide or potassium hydroxide, and more preferably, potassium hydroxide.

Examples of polar aprotic solvents include, but are not limited to, dimethyl sulfoxide (DMSO), N-methyl pyrrolidone (NMP), dimethylformamide (DMF), and the like. Preferably, the polar aprotic solvent is DMSO. Mixtures of polar aprotic solvents may also be used. Mixtures of these polar aprotic solvents with organic solvents such as toluene, chlorobenzene, and heptane may also be used.

Once the substitution reaction is complete, the reaction mixture is neutralized and the resulting ortho-nitroalkyl nitroarene compound (II) is extracted into an aromatic or aliphatic organic solvent. Examples of the organic solvent include, but are not limited to, toluene, chlorobenzene, heptane and mixtures thereof.

Oxidizing ortho-nitroalkyl nitroarene compound (II) via an oxidative Nef reaction yields an ortho-nitroaryl ketone of formula (III):

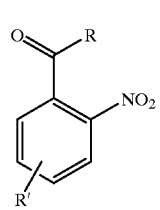

(III)

where R and R' are as defined above.

The oxidative Nef reaction may be conducted in either a single phase aqueous alkaline system or in a biphasic system of an aqueous alkaline solution and a water-immiscible organic solvent. The aqueous alkaline solution may be an aqueous solution of an alkali or alkaline earth metal carbonate. The alkali metal of the carbonate may be any alkali metal including, for example, sodium, potassium, cesium and the like. Preferably, the alkali metal is sodium or potassium. More preferably, the alkali metal is potassium. The alkaline earth metal of the carbonate may be any alkaline earth metal including, for example, magnesium, calcium and the like. Examples of a suitable aqueous alkaline solution include, but are not limited to, aqueous solutions of at least one of the following carbonates: sodium carbonate, potassium carbonate, cesium carbonate, magnesium carbonate and calcium carbonate. Preferably, the aqueous alkaline solution is an aqueous solution of potassium carbonate.

Examples of the water-immiscible organic solvent include, but are not limited to, toluene, chlorobenzene, heptane and mixtures of such solvents. Preferably, the organic solvent is the solvent used to extract the ortho-nitroalkyl nitroarene compound (II). The oxidation may be accomplished using any oxidant known in the art. Examples of the oxidant include, but are not limited to, hydrogen peroxide, potassium permanganate, and ammonium persulfate. Preferably, the oxidant is hydrogen peroxide. Preferably, the ratio of hydrogen peroxide:potassium carbonate:ortho-nitroalkyl nitroarene compound (II) is 4.0:2.5:1, more preferably 3.75:2.25:1 and most preferably 3.5:2:1.

Another embodiment of the invention is a process for the preparation of ortho-thioether-substituted aromatic ketones.

The process contacts an aromatic ketone having a nitro group ortho to the keto group with a thiolate anion, optionally in the presence of a catalyst. The reactants may be combined in any order of addition. Preferably, the thiolate anion is added to the aromatic ketone or a mixture of the aromatic ketone and catalyst. This process, along with preferred embodiments, is described in more detail in the discussion and examples below.

To prepare an ortho-thioether-substituted aromatic ketone, the process of the invention reacts an ortho-nitroaryl ketone (III) with a thiolate anion, optionally in the presence of a catalyst, to produce an ortho-thioether aromatic ketone of formula (IV):

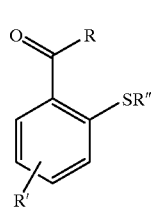

(IV)

In formula (IV), R and R' are as defined above. R" is a substituted or unsubstituted $C_1$–$C_{10}$ alkyl, $C_6$–$C_{10}$ aryl, or $C_4$–$C_{10}$ heteroaromatic group. Preferably, R" is a methyl group.

The pH of an ortho-nitroaryl ketone (III) reaction mixture is inherently neutral. As thiolate anion concentration increases within the reaction mixture, the pH of the reaction mixture may become basic, generally, greater than about 11.7. In a preferred embodiment, the pH of the mixture may be lowered by the addition of a neutralizing agent such as, for example, sodium bicarbonate. The pH of the reaction mixture may be lowered to the point of methyl mercaptan formation. Preferably, the pH may be lowered to about 11.4. The pH may be maintained at the lowered pH by the addition of a buffer or buffering agents known in the art such as, for example, boric acid, glycine, and phosphate buffers.

The thiolate anion may be an alkali metal or alkaline earth metal, each as defined above, salt of a thiol. The thiol may be a substituted or unsubstituted $C_1$–$C_{10}$ alkyl, $C_6$–$C_{10}$ aryl, or $C_4$–$C_{10}$ heteroaromatic thiol. Alkyl, aryl and heteroaromatic are each as defined above. Examples of suitable thiolate anions include, but are not limited to, sodium thiomethoxide, potassium thiomethoxide, and the like.

The catalyst may be a tetraalkylammonium or tetraalkylphosphonium salt. Examples of the catalyst include, but are not limited to, tetrabutylammonium bromide, tetrabutylammonium hydrogen sulfate, methyltributylammonium chloride, tetrabutylphosphonium bromide, and tricaprylylmethylammonium chloride (i.e. ALIQUAT ® 336 available from Aldrich Chemical Co., Milwaukee, Wis.). Preferably, the catalyst is a bromide salt. More preferably, the catalyst is tetrabutylammonium bromide. The amount of catalyst used is between 5–20 mol % based on the ortho-nitroaryl ketone (III). As a preferred embodiment, the presence of the catalyst provides yields of about >90% and selectivity of about >98%.

The process is preferably conducted using a catalyst under phase-transfer conditions, i.e. in a mixture of water and at least one water-immiscible organic solvent. Examples of water-immiscible organic solvents include, but are not limited to, toluene, chlorobenzene, heptane, and mixtures of these solvents. Generally, the product of the process may be isolated from the organic phase.

The process to prepare an ortho-thioether aromatic ketone of formula (IV) may also be conducted in water, a water-miscible polar aprotic organic solvent, or a mixture of solvents and water. Examples of the water-miscible polar aprotic organic solvent include, but are not limited to, acetone, THF, DMF and the like.

Still another embodiment of the invention is a process for the preparation of an aromatic ketone having a thioether group ortho to the keto group. This process advantageously combines the processes described above into a single synthesis. According to the invention, in a single synthesis, intermediates need not be isolated. Rather, the reaction mixture containing the intermediate may be used in a subsequent reaction step(s). Preferably, the single synthesis is a one-pot synthesis as understood by those of skill in the art. The process contacts a halonitroarene compound having a halo group ortho to a nitro group (I) with a nitroalkane (Ia) in a polar aprotic solvent and in the presence of a hydroxide base to produce an ortho-nitroalkyl nitroarene compound (II). The process also involves oxidizing the ortho-nitroalkyl nitroarene (II) compound to produce an aromatic ketone having a nitro group ortho to a keto group (III). Contacting an aromatic ketone having a nitro group ortho to a keto group (III) with a thiolate anion, optionally in the presence of a catalyst, produces the aromatic ketone having a thioether group ortho to the keto group (IV). The steps in this process, along with preferred embodiments, are the same as those described above.

A further understanding can be obtained by reference to certain specific examples which are provided herein for purpose of illustration only and are not intended to be limiting unless otherwise specified.

EXAMPLES

Example 1

3-Nitro-4-(1-nitroethyl)benzotrifluoride (2):

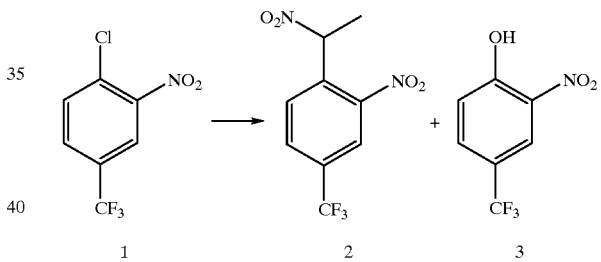

Potassium hydroxide pellets (8.42 g; 0.150 mol; 3 equiv) were crushed and placed in a 250-mL 3-necked flask equipped with a thermometer and an addition funnel. Reagent-grade DMSO (25 mL) was added and the mixture vigorously stirred. An ice-water cooling bath was then applied and when the temperature of the reaction mixture had cooled to 19° C. a mixture of nitroethane (3.95 mL; 0.055 mol; 1.1 equiv) and 4-chloro-3-nitrobenzotrifluoride (1; 7.46 mL; 0.050 mol) were added to the reaction mixture (addition funnel) over 15 min at a rate such that a temperature of 15–20° C. was maintained. After the addition was complete, the reaction mixture was cooled to 15° C. and the ice bath was replaced with a cool water bath (10–15° C.) and the reaction mixture was allowed to warm to 20° C. over 2 h, at which time GC analysis indicated >98% consumption of 1 and a ratio of 2:3 of 98:2. Toluene (25 nL) was added and the reaction mixture was cooled in ice-water. Aqueous hydrochloric acid (6 N; 15 mL; 0.090 mol) was added dropwise with vigorous stirring at such a rate that the temperature remained below 20° C. Water (40 mL) was then added and the layers were allowed to separate for 10 min. The bottom aqueous layer was decanted, and the top organic solution was used directly for the next step. An aliquot of this organic solution was analyzed by $^1$H NMR and indicated a 96:4 ratio of 2:3.

2: $^1$H NMR (CDCl$_3$) δ 8.349 (s, 1H); 7.976 (dd, 1 H, J=1.71, 8.24 Hz); 7.788 (d, 1H, J=8.24 Hz); 6.296 (q, 1H, J=6.96 Hz); 2.036 (d, 3H, J =6.78 Hz). GC (30 m DB-17, 100° C., 3 min; 100–280° C., 15°/min; 280° C., 1 min): $t_R$ 10.71 min 3: $^1$H NMR (CDCl$_3$) δ 10.815 (s, 1H); 8.435 (d, 1H, J=1.77 Hz); 7.830 (dd, 1H, J=2.19, 8.79 Hz); 7.315 (d, 1H, J=8.91 Hz). GC (30 m DB-17, 100° C., 3 min; 100–280° C., 15°/min; 280° C., 1 min): $t_R$ 5.53 min Comparative Example 1
4-Methoxy-3-nitrobenzotrifluoride (6):

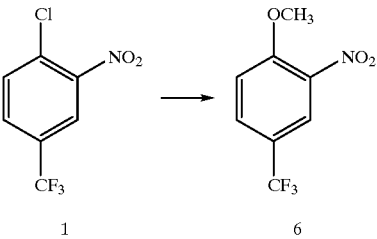

Sodium methoxide (1.35 g; 25 mmol; 2.5 equiv) was slurried in DMSO (10 mL) and cooled in a cool water bath. Nitroethane (0.79 mL; 11 Immol; 1.1 equiv) and 4-chloro-3-nitrobenzotrifluoride (1; 1.49 mL; 10 mmol) were mixed and added slowly dropwise with cooling such that the temperature remained between 15 and 20° C. After the addition was complete, the reaction mixture was allowed to warm slowly over 3 h from 15 to 18° C. and then stirred overnight at 18° C. to completely consume 1 according to GC analysis. Toluene (10 mL) was added and the mixture was cooled in ice water and 3 N HCl (10 mL; 30 mmol; 3 equiv) was added dropwise such that the temperature remained below 20° C. After the addition the layers were separated, and the organic solution was dried (Na$_2$SO$_4$) and concentrated to afford 2.60 g of crude product. Analysis of this material by $^1$H NMR and GC indicated that the major product was 6 with 2 and 3 as minor products.

6: $^1$H NMR (CDCl$_3$) δ 8.127 (d, 1H, J=1.8 Hz); 7.803 (dd, 1H, J=2.1, 8.7 Hz); 7.203 (d, 1H, J=9.06 Hz); 4.028 (s, 3H). GC (30 m DB-17, 100° C., 3 min; 100–280° C., 15°/min; 280° C., 1 min): $t_R$ 9.35 min Comparative Example 2
4-tert-Butyl-3-nitrobenzotrifluoride (7):

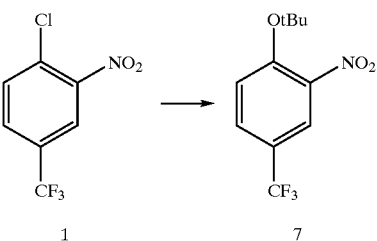

Potassium tert-butoxide (2.81 g; 25 mmol; 2.5 equiv) was dissolved in tetrahydrofuran (10 mL) and cooled to 0° C. Nitroethane (1.08 mL; 15 mmol; 1.5 equiv) was added dropwise and 4-chloro-3-nitrobenzotrifluoride (1; 1.49 mL; 10 mmol) was then added dropwise. A vigorous reaction ensued and the reaction mixture turned red-brown. The reaction mixture was stirred at ambient temperature for 2 h at which point 1 had been completely consumed (GC analysis). The reaction mixture was neutralized by the addition of 3 N HCl (15 mL) and extracted with ethyl acetate (3×15 mL). The combined extracts were dried (MgSO$_4$) and concentrated to afford 7 as the major product (along with phenol 3) by $^1$H NMR analysis. $^1$H NMR (CDCl$_3$) δ 7.986 (d, 1H, J=2.20 Hz); 7.709 (dd, 1 H, J=2.51, 8.79 Hz); 7.342 (d, 1H, J=8.79 Hz); 1.500 (s, 9H).

Example 2
2-Nitro-4-trifluoromethylacetophenone (4):

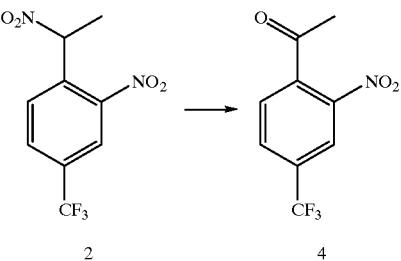

To the organic solution from Example 1 at ambient temperature (25° C.) was added a solution of potassium carbonate (13.82 g; 0.10 mol; 2 equiv) in water (15.6 mL) with vigorous stirring. Aqueous hydrogen peroxide (35%; 15.5 mL; 0.175 mol; 3.5 equiv) was added dropwise over 15 min such that the temperature was maintained below 30° C. The reaction mixture was stirred and allowed to self-heat with intermittent water bath cooling such that the temperature remained below 30° C. The reaction mixture was stirred for 17 h to completely consume 2 according to GC analysis. Acetic acid (1–2 mL) was added to afford a pH of 7–8. Stirring was stopped and the layers were allowed to separate. The bottom aqueous layer was removed and discarded, and the organic solution was washed with 1 M sodium thiosulfate (10 mL). The bottom aqueous layer was discarded, and the organic layer was removed, dried (Na$_2$SO$_4$), and concentrated to afford 10.51 g of 4 which was 88.85% pure by quantitative GC analysis (vs. internal standard) to afford an overall 80% yield of 4 from 1. Alternatively, the organic solution of 4 could be taken directly to the next reaction.

4: $^1$H NMR (CDCl$_3$) δ 8.408 (s, 1H); 8.000 (dd, 1H, J=1.47, 8.67 Hz); 7.583 (d, 1H, J=8.25 Hz); 2.600 (s, 3H). GC (30 m DB-17, 100° C., 3 min; 100–280° C., 15°/min; 280° C., 1 min): $t_R$ 8.77 min.

Example 3
2-Thiomethyl-4-trifluoromethylacetophenone (5):

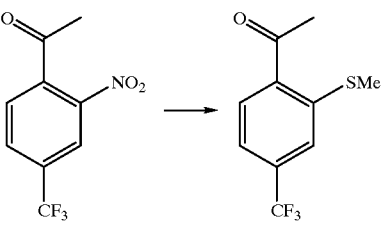

Sodium thiomethoxide (3.60 g; 51.3 mmol; 1.7 equiv) was dissolved in 13.5 mL of water. This resulting solution was cooled to 20° C. and tetrabutylammonium bromide (1.32 g; 4.11 mmol; 0.14 equiv) was added. A solution of acetophenone 4 (83.8% assay; 8.31 g; 29.9 mmol) in toluene (17 mL) was added over one minute to the reaction mixture, and an exotherm to 27° C. was noted. The reaction mixture immediately turned dark and was cooled to 20° C. and stirred for 1 h to completely consume 4 (GC analysis) and afford >98% selectivity to 5. Stirring was stopped and the layers were allowed to separate. The bottom aqueous layer was removed and the upper organic layer was washed with 3 N HCl (2×10 mL) and saturated NaHCO₃ (5 mL). The organic solution was dried (MgSO₄) and concentrated. The residue was dissolved in 1:1 toluene:heptane, washed with water, dried (Na₂SO₄), and concentrated to afford 7.84 g of crude 5. Quantitative GC analysis using an internal standard indicated 86.14% purity for the crude 5 to afford a 96.5% yield.

$^1$H NMR (CDCl₃) δ 7.926 (d, 1H, J=8.12 Hz); 7.525 (s, 1H); 7.435 (dd, 1H, J=1.40, 8.36 Hz); 2.657 (s, 3H); 2.480 (s, 3H). $^{13}$C NMR (CDCl₃) δ 198.9, 144.4, 137.3, 134.1 (q, J=32.2 Hz), 131.6, 125.8, 122.1 (q, J=3.7 Hz); 120.6(q, J=3.4 Hz),28.8, 16.4. FDMS m/e 234 (M⁺). GC (30 m DB-17, 100° C., 3 min; 100–280° C., 15°/min; 280° C., 1 min): $t_R$ 10.14 min.

Example 4
Single-Phase Preparation of 2-Thiomethyl-4-trifluoromethyl-acetophenone (5):

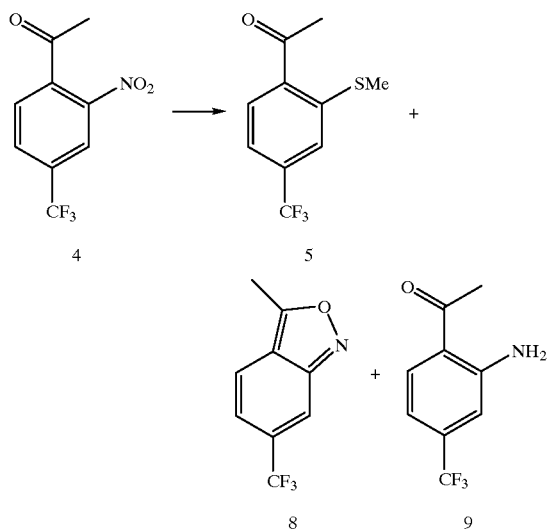

Acetophenone 4 (81.1%; 4.66 g; 6.2 mmol) was dissolved in dimethyl formamide (40 mL) and cooled to 10° C. Sodium thiomethoxide (1.68 g; 24 mmol; 1.5 equiv) was dissolved in water (20 mL) and was added over approximately 30 min such that the temperature of the reaction mixture remained below 10° C. After the addition was complete, the reaction mixture was warmed to room temperature. GC analysis of the reaction mixture indicated complete consumption of 4 and formation of products 5 and 8 in a ratio of 96:4 along with a very small amount of 9. The reaction mixture was diluted with water (100 mL) and cooled to 5c for 30 min. The resulting precipitate was filtered, washed with water, and air-dried to afford 2.54 g of 5 which was 97.1% pure (Quantitative GC) to afford a 65% yield of 5.

The claimed invention is:

1. A process for preparing an aromatic ketone having a nitro group ortho to the keto group, the process comprising the steps of:

contacting a halonitroarene compound, wherein the halo group is ortho to the nitro group on the aromatic ring, with a nitroalkane in a polar aprotic solvent and in the presence of a hydroxide base under conditions sufficient to produce an ortho-nitroalkyl nitroarene compound; and oxidizing said ortho-nitroalkyl nitroarene compound under conditions sufficient to produce the aromatic ketone.

2. A process of claim 1, wherein said hydroxide base is selected from the group consisting of potassium hydroxide and sodium hydroxide.

3. A process of claim 1, wherein said hydroxide base is potassium hydroxide.

4. A process of claim 1, wherein said polar aprotic solvent is selected from the group consisting of dimethyl sulfoxide, tetrahydrofuran, N-methyl pyrrolidone and dimethylformamide.

5. A process of claim 4, wherein said polar aprotic solvent is dimethyl sulfoxide.

6. A process of claim 1, wherein said oxidizing step comprises the step of subjecting said ortho-nitroalkyl nitroarene compound to an oxidative Nef reaction.

7. A process of claim 1, wherein said oxidative Nef reaction is conducted in a single phase aqueous alkaline system or in a biphasic system of an aqueous alkaline solution and a water-immiscible organic solvent in the presence of an oxidant selected from the group consisting of hydrogen peroxide, potassium permanganate, and ammonium persulfate.

* * * * *

UNITED STATES PATENT AND TRADEMARK OFFICE
CERTIFICATE OF CORRECTION

PATENT NO. : 6,096,929  
DATED : August 1, 2000  
INVENTOR(S) : Neil W. Boaz

Page 1 of 1

It is certified that error appears in the above-identified patent and that said Letters Patent is hereby corrected as shown below:

<u>Title page,</u>  
Item [73], the Assignee should read -- Eastman Chemical Company -- not "Eastman Kodak Company".

Signed and Sealed this

Twenty-seventh Day of August, 2002

*Attest:*

*Attesting Officer*

JAMES E. ROGAN  
*Director of the United States Patent and Trademark Office*